United States Patent [19]
DiResta

[11] 4,445,515
[45] May 1, 1984

[54] APPARATUS FOR PERFORMING TISSUE PERFUSION MEASUREMENTS

[76] Inventor: Gene R. DiResta, 2 Hudson View Dr., Yonkers, N.Y. 10701

[21] Appl. No.: 317,515

[22] Filed: Nov. 2, 1981

[51] Int. Cl.³ .............................................. A61B 5/00
[52] U.S. Cl. .................................... 128/632; 128/635
[58] Field of Search ............... 128/1 R, 632, 633, 635, 128/630, 634; 73/73, 861.02, 861.08, 432 R

[56] References Cited

U.S. PATENT DOCUMENTS 4,016,863  4/1977  Brantigan ............................ 128/632
4,244,713  1/1981  Goodwin ............................ 128/632

OTHER PUBLICATIONS

"Chem. Abstracts", vol. 80, 1974, p. 187 Abstract #117800D.
"Naturwissenschaften", 1970, vol. 57, p. 311.
"Determination of Local blood Flow . . . ", Pflugers Arch. 348, pp. 225-238 (1974).
Akademie der Wissenschaften, Wodick, 1976, pp. 249-251 and 334-355.
"Evaluation of Local Tissue Blood Flow . . . ", J. Appl. Physiol, Levy et al.
"Thermodynamic Technique for the Quantification of Regional Blood Flow", Adams et al., Amer. J. of Physiol, 1980.
"Process Systems Analysis and Control", McGraw Hill, Coughanowr et al.

Primary Examiner—C. Fred Rosenbaum
Assistant Examiner—T. J. Wallen

[57] ABSTRACT

Apparatus and method are disclosed for monitoring the perfusion rate of a liquid through the tissue of a living animal. The apparatus and method involve contacting the tissue with an electrode probe and at least one sensor probe at a predetermined spaced relation to the electrode probe. A continuous electrical current is applied to the electrode probe to generate in situ in the tissue a gaseous substance the concentration of which may be measured by the sensor member. The electrical current is applied at a rate which maintains the concentration at a selected level, the perfusion rate being derived as a function of the quantum of electrical current required to be applied. The diffusion rate of the substance through the fluid may be mathematically derived through the use of additional sensor probes and the diffusion rate may be subtracted from the measured perfusion rate. In this manner a constant monitoring of perfusion rate is obtained.

6 Claims, 14 Drawing Figures $P(S_2) > P(S_1)$
$P(S_1) > P(S_3)$
$R_1 > R_2$

APPARATUS FOR PERFORMING TISSUE PERFUSION MEASUREMENTS

TECHNICAL FIELD

The invention relates to an apparatus and method for the measurement of perfusion within living tissues; measurement is made by using a probe to electrochemically generate and emit hydrogen into the tissue and a polarigraphic probe to measure the concentration of hydrogen at a point a known distance from the hydrogen source.

BACKGROUND ART

Perfusion measurements attempt to determine the quantity of blood moving through a capillary network of a volume of tissue. The ability to perform tissue perfusion measurements, on a continuous basis, with accuracy and safety is important to both the clinical and research branches of the medical community because of the fundamental role perfusion plays in physiological processes. Likewise, perfusion measurements are of value in assessing the state of diseased tissue. While existing techiniques for performing perfusion measurements fall into a number of categories, measurements are, generally, made by monitoring the movement of an indicator through the tissue's capillary network. In such systems the concentration of the indicator at a point of known distance from the source may be employed in a mathematical model of the indicator diffusion system to derive the perfusion of the tissue volume.

The existing measuring methodology can be divided into two categories, namely, those which provide steady-state values and those which provide continuous values. Steady-state techniques are those which require that the perfusion within the tissue volume to be examined remain unchanged during the time required to perform a measurement. Continuous techniques permit the observation and measurement of perfusion transients.

The steady-state category includes methods which permit only one measurement per subject, e.g., $C^{14}$-antipyrine autoradiographic methods and those which permit multiple measurements. These methods require minutes per measurement to be performed, e.g., inert gas clearance, $H_2$-short interval clearance, positron emission tomography, microsphere entrapment, and thermal clearance. Selection of a method from this category depends upon the size of the measurement volume for which the perfusion measurement is to be made, subject safety, measurement time required and equipment requirements, e.g., the autoradiographic method permits the smallest volume resolution, requires the longest measurement time (about two weeks per measurement) and that the subject is destroyed to perform the measurement.

Continuous techniques attempt to read transient changes in perfusion. This category includes the laser doppler method, the nuclear magnetic resonance method, video image analysis and heated probe methods. The first two mentioned techniques permit perfusion measurement non-invasively; however the measurement volumes are large. The video method is useful for surface capillary network perfusion measurements. The heated probe techniques measure perfusion from small volumes, cause minor tissue damage and require minimal instrumentation.

As can be seen from the above discussion, the above techniques suffer from one or more of a number of serious problems, including, inability to deal with small volumes, tissue damage, a requirement for extensive instrumentation, long measurement time and the like.

DISCLOSURE OF THE INVENTION

The invention, as claimed, is intended to provide a remedy. It solves the problem of how to measure perfusion on a continuous basis in very small tissue volumes, while causing minimal or no tissue damage and with a minimum of instrumentation. The device and method of the present invention are capable of making transient flow measurements, steady-state flow measurements and measurements under a wide variety of tissue conditions. Moreover, these measurements may be made within a minimum measurement interval on the order of twenty to thirty seconds.

Generally, the method of the present invention, which shall be referred to herein as the $H_2$-clamp performs perfusion measurements by relating the current required to maintain a steady-state concentration of $H_2$ at a point removed from the point of generation to an effective diffusion coefficient.

Generally the $H_2$-clamp method derives perfusion measurements from transport phenomena which include diffusive and convective processes. These processes are incorporated into a mathematical model of the system and a mathematical description of the measurement approach and the tissue capillary network's response. These models may be used to relate the known concentration at a point removed from the point of $H_2$ generation and the amount of $H_2$ being generated to derive the perfusion through the system.

In accordance with the method of the present invention, an effective technique is also provided for avoiding the problem common to all perfusion measurements, namely, the unknown geometry of the tissue-capillary network and the variations of that geometry in response to the perfusion which one desires to measure. Moreover, because of the small tissue volumes (on the order of 0.1 mm.$^3$) the method of the present invention is capable of measuring micro-perfusion.

BRIEF DESCRIPTION OF DRAWINGS

One way of carrying out the invention is described in detail below with reference to drawings which illustrate only one specific embodiment, in which.

BEST MODE FOR CARRYING OUT THE INVENTION

Figure 1:
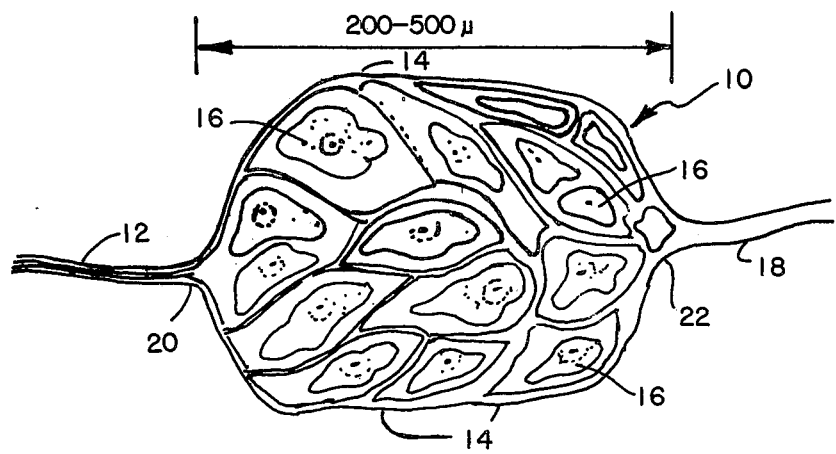
FIG. 1 is a diagramatic illustration of a volume of tissue.

Referring to FIG. 1 a volume of tissue 10, the perfusion of which may be measured in accordance with the method and apparatus of the present invention, is illustrated. The volume of tissue 10 is fed with oxygen bearing blood by an arteriole 12 which feeds the blood to a system of capillaries 14 which provide the oxygen bearing blood to a matrix of cells 16. After the blood has performed its function of providing oxygen to the cells 16, the capillaries 14 come together to exhaust blood into a venule 18. For purposes of illustration, the oxygen bearing blood is illustrated as black in the arteriole 12 and becoming progressively lighter in shade as it proceeds toward the venule 18.

Typically, in animal tissue, the distance between the output 20 of an arteriole 12 and the input 22 of a venule 18 is on the order of two to five hundred microns. Some idea of the scale of the method of the present invention may be obtained from the fact that it is expected that effective measurement of volumes as low as 0.1 mm.$^3$ are possible. Likewise, measurements have been taken in time intervals on the order of twenty to thirty seconds, using a probe having a dimension of 150-175 microns of separation between the $H_2$ generator and sensor.

Figure 2:
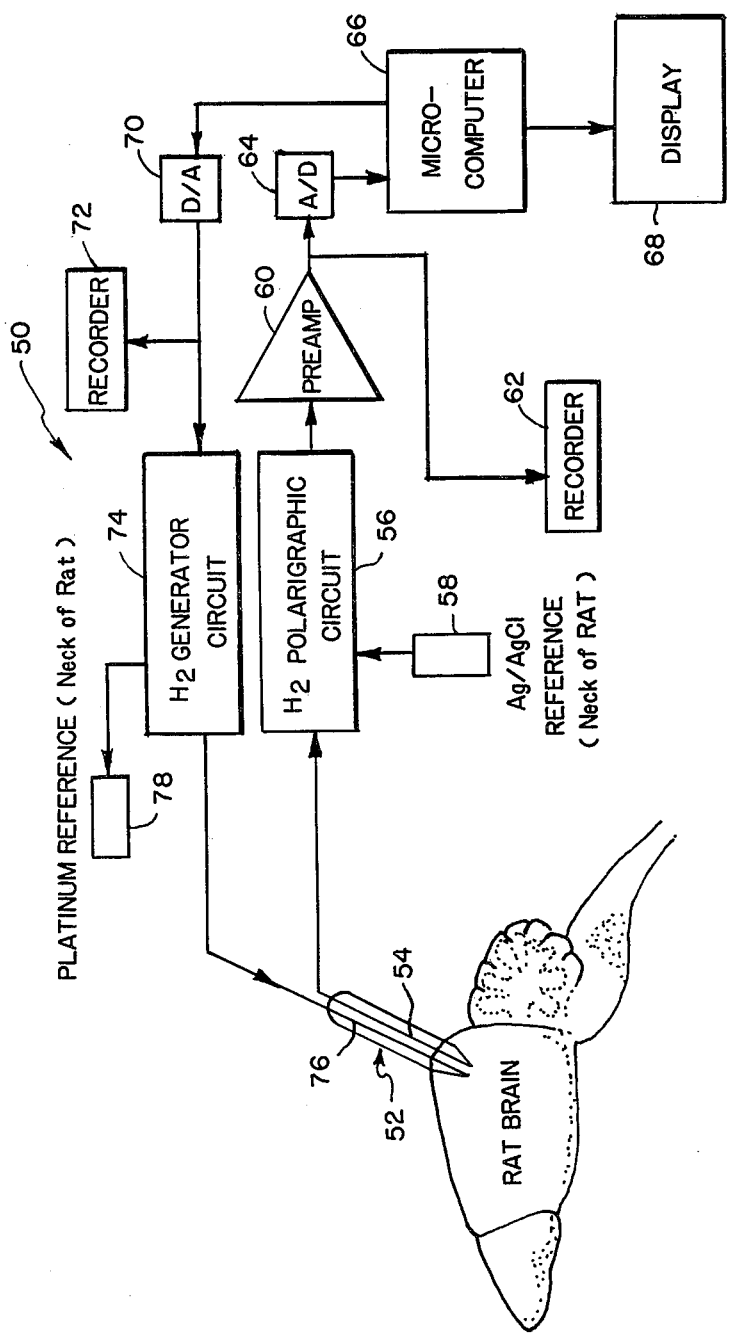
FIG. 2 is a schematic diagram of a system for measuring perfusion in accordance with the present invention.

A system constructed in accordance with the present invention is illustrated in FIG. 2. The perfusion measurement system 50 comprises a measurement probe 52 which includes an $H_2$ sensing wire 54. $H_2$ sensing wire 54 is in turn coupled to an $H_2$ polarigraphic measurement device 56 which is a differential metering device. Measurement device 56 is also responsive to an AgCl reference probe 58. The output of measurement device 56 is sent to a preamplifier 60 whose output in turn drives a recorder 62. The output of preamp 60 also drives an analog-to-digital converter 64 which in turn provides its output to a micro-computer 66. The output of micro-computer 66 drives a display 68 which displays a numerical measurement of perfusion being measured by probe 52. Micro-computer 66 also drives a digital-to-analog device 70. The output of digital-to-analog device 70 is in turn coupled to a recorder 72 which records the analog value produced by the micro-computer 66. The output of the digital-to-analog converter 70 is also sent to a hydrogen generating circuit 74 which, in turn, is coupled to an $H_2$ generating wire 76. Inasmuch as the hydrogen generating circuit operates electrochemically it is also coupled to a reference electrode 78.

Figure 3:
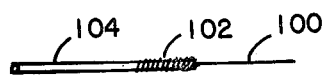
FIGS. 3–7 illustrate successive steps in the manufacture of a single sensor probe useful in the present invention.
Figure 4:
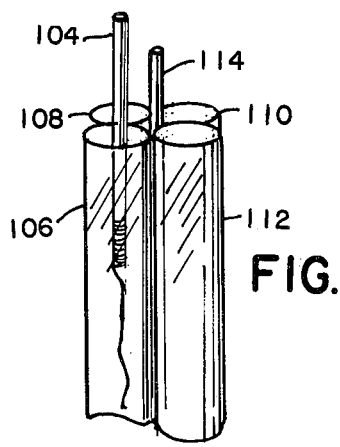
Figure 5:
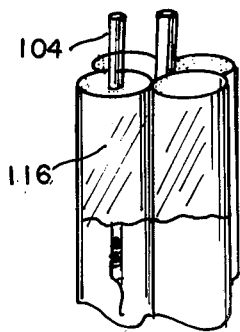

Manufacture of a probe 52 useful in conjunction with the present invention may be carried out in accordance with the process steps illustrated in FIGS. 3-7. As shown in FIG. 3, a length of fine platinum wire 100 having a thickness on the order of 15 microns is wound in several turns 102 around a length of platinum wire 104 having a length of several centimeters and a thickness on the order of 125 microns. The assembly illustrated in FIG. 3 is then placed into one capillary tube 106 in a cluster of four glass capillary tubes which includes capillary tube 106 as well as tubes 108, 110 and 112. A second length 114 of platinum wire having a thickness on the order of 125 microns is then placed in the center space defined by the four barrel capillary assembly, as illustrated in FIG. 4. Epoxy resin 116 is then placed into the ends of the capillary tubes 106-112 and extends from their ends into the tubes a distance of about 0.6 cm., as illustrated in FIG. 5.

Figure 6:
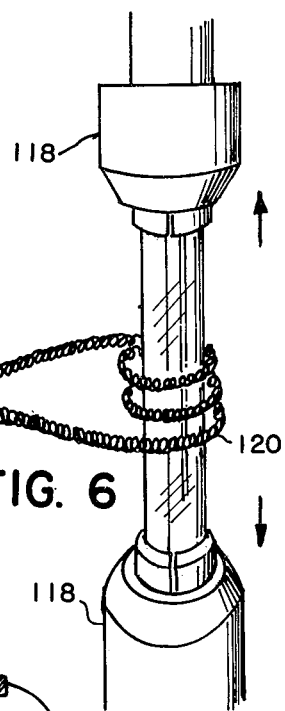

The assembly illustrated in FIG. 5 is then grasped at its ends by a pair of holders 118, as illustrated in FIG. 6.

A heater coil 120 is disposed around the capillary tube in order to melt the glass. The holders of the capillary puller are then pulled away from each other thus drawing the capillary. It has been found useful that increasing the heat applied to the capillary during drawing will insure that the proper glass to platinum wire union is obtained. Likewise, positive gripping of the capillary tube assembly by holders 118 can be insured by sanding the ends of the assembly.

Figure 7:
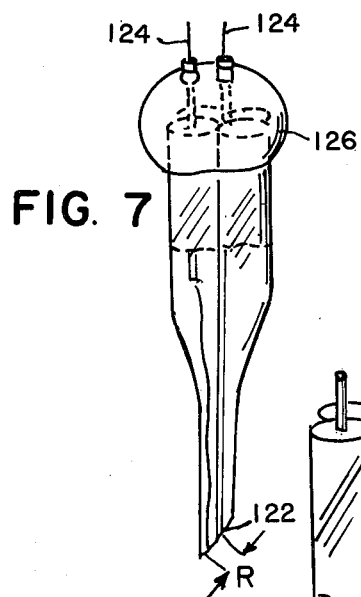

After the pulling has been completed, the assembly is cut and bevelled to a slanted surface 122, as illustrated in FIG. 7. Likewise, end connectors 124 are secured to wires 108 and 114 and the mechanical integrity of the system is improved by application of a quantity of epoxy resin 126 to the assembly. The probe illustrated in FIG. 7 is then ready for use in measuring diffusion in porous structures where the probe must perform a piercing entry in order to reach the area where the measurement is desired.

Figure 8:
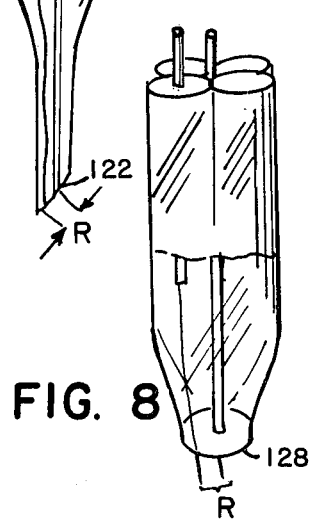
FIGS. 8–9 illustrate successive steps in the manufacture of an alternative probe useful in the apparatus of the present invention.
Figure 9:
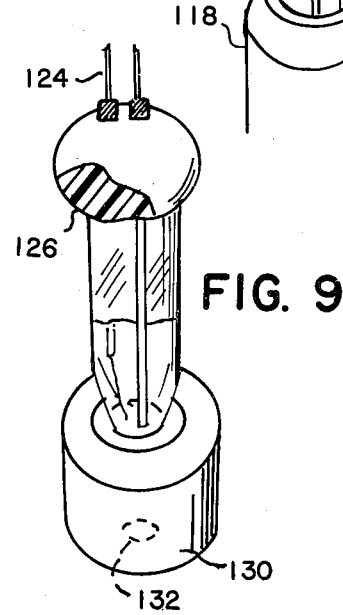

Alternatively, the assembly shown in FIG. 7 may be bevelled to a flat tip surface 128, as illustrated in FIG. 8 and the assembly completed by the addition of epoxy 126 and end connectors 124 as well as a housing 130 which has an undersurface 132 which is substantially smooth and lies in the same plane as the surface 128 of the probe. Such a probe is illustrated in FIG. 9 and is particularly useful in situations where diffusion is measured from the surface of a porous structure.

Figure 10:
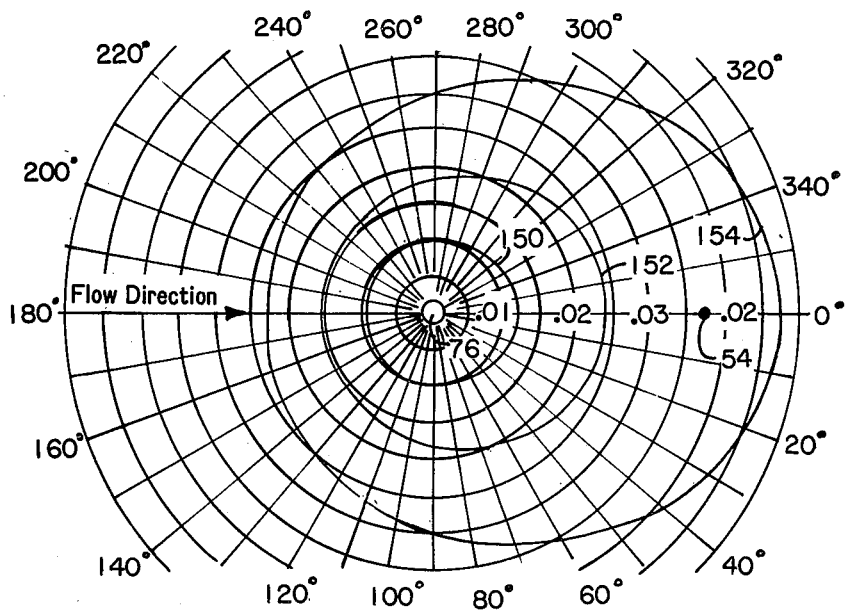
FIG. 10 illustrates surfaces of equal hydrogen concentration surrounding a hydrogen source in tissues.

Referring back to FIG. 2, the operation of the circuit involves the generation of hydrogen at the $H_2$ generating wire 76. The amount of hydrogen is generated in response to measurements made by the circuit illustrated in FIG. 2 as will be described below. As shown in FIG. 10, if the $H_2$ point source is placed at the origin of the graph, hydrogen will be dispersed into the porous structure with an area of high hydrogen concentration defined by line 150 a region of lower concentration defined by line 152 and a region of still lower concentration defined by line 154. The concentration of $H_2$ will be detected by $H_2$ sensing wire 54 which will detect the hydrogen concentration polarigraphically with reference to a reference probe which is placed into electrical contact with the porous body through which perfusion is being measured but outside the path of the flow diffusing through the subject porous structure. The output of the polarigraphic measurement device 56 then drives a preamp 60 which in turn sends a signal indicative of hydrogen concentration to recorder 62. As illustrated qualitatively in FIG. 10 and as will be described in detail below, the rate of flow will cause hydrogen to be more concentrated in the direction toward which the flow is directed. Moreover, the rate of flow will affect the concentration at any given point where the sensing wire 54 is placed.

The output of preamp 60 is also sent to an analog-to-digital converter 64 which provides a signal indicative of hydrogen concentration to a microcomputer 66. In response to this signal microcomputer 66 produces a digital signal which is provided to digital-to-analog converter 70 which, in turn, provides an analog signal to the hydrogen generator circuit 74, causing it to generate hydrogen. Micro-computer 66 is so programmed as to cause the generator circuit 74 to generate enough hydrogen to maintain the amount of hydrogen detected by measurement device 56 at a constant level. The effectiveness of this function may be monitored by recorder 62.

In view of the fact that the hydrogen concentration is a function of the rate of flow, and hence the perfusion through the porous structure, the amount of hydrogen which the generating wire 76 must generate to maintain a steady concentration at the sensing location may be used as an indication of the perfusion of the device. For example, if perfusion is at a very high rate, large amounts of hydrogen generated by wire 76 will be carried away quickly and concentrations around wire 54 (FIG. 10) will be relatively low, thus requiring generation of greater amounts of hydrogen to maintain the desired level of steady-state hydrogen concentration around wire 54. On the other hand, if the rate of flow is very low a very small amount of hydrogen generated by wire 76 will maintain the desired steady-state level of hydrogen adjacent the sensing wire 54. Thus, recorder 72 effectively records the perfusion of water through the structure into which the probe is inserted. As noted above, insertion of such a probe into the structure is most convenient with a probe such as that illustrated in FIG. 7. Alternatively, perfusion on the surface may be measured using the probe illustrated in FIG. 9.

Given a set of parameters which describe a porous structure, the H$_2$ clamp device relates by an appropriate mathematical model the current required to maintain a steady-state concentration of H$_2$ at a measuring site located R microns away from a generating site to the diffusive convective losses occurring in the region between these points. Mathematical models have been developed from two view points, a more precise distributed parameter approach and a simpler lumped parameter approach. Equation 1 results from the distributed approach while Equation 2 results from the lumped approach.

$$\partial P/\partial t = \nabla \cdot (D^* \nabla P) - \nabla \cdot (P\bar{f}) \quad (1)$$

$$\frac{dRp}{dt} + \frac{K}{V} * Hp - \frac{k}{V} Ht = \frac{G}{V}(t - \theta) \quad (2)$$

Equation 1, although more descriptive, requires simplifying assumptions to make it practical. Equation 3 is the simplified form of Equation 1 developed by assuming that the tissue properties are homogenous in the region of interest and that the perfusion moves in only one direction through this region.

$$\partial P/\partial t = D^* \nabla^2 P - \bar{f}(\partial P/\partial x) \quad (3)$$

The working equations which are used in the implementation of the invention to perform a perfusion measurement includes the time dependent solution of Equation 2 (Equation 5, below) and the steady-state solution of Equation 3 which is Equation 4, below.

$$P = \frac{Qe^{-\bar{f}(R-x)/2D^*}}{4\pi D^* R} \quad (4)$$

$$P(t) = P(t_\infty)(1 - e^{-(t-\theta)/\tau}) \quad (5)$$

Figure 12:
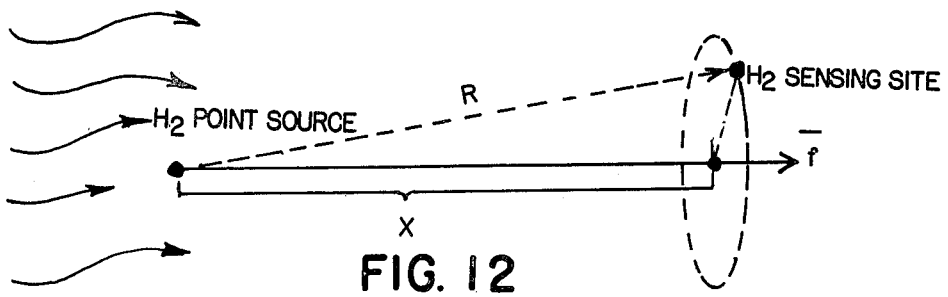
FIG. 12 is a diagramatic representation useful in explaining the use of the mathematical model of Equation 4 in conjunction with the probes illustrated in FIGS. 7 and 9.

Equation 4 is the relationship which is used to calculate perfusion, $\bar{f}$, while Equation 5 is used by the instrument to perform continuous measurements. (Equation 5 can also be used to determine perfusion, however, the units of the measurement are different. Perfusion, F, determined with Equation 5 has units of volume/time and is a volumetric flow rate while perfusion determined with Equation 4, $\bar{f}$, has units of length/time and is a linear flow rate.) Equation 4 determines the concentration profile of H$_2$ in the region surrounding the generation site and requires D*, the magnitude of effective diffusion coefficient, $\bar{f}$, mean perfusion; Q, the H$_2$ generation rate; and X, the position of the sensor relative to the direction of perfusion. This arrangement is displayed in FIG. 12. This last requirement is eliminated when the sensor is placed in the direction of the flow. The hydrogen concentration measured at this point is at a maximum, however, perfusion can not be determined. The action of finding the maximum H$_2$ concentration, alters Equation 4 resulting in Equation 6.

$$P = Q/(4\pi D^* R) \quad (6)$$

Figure 14:
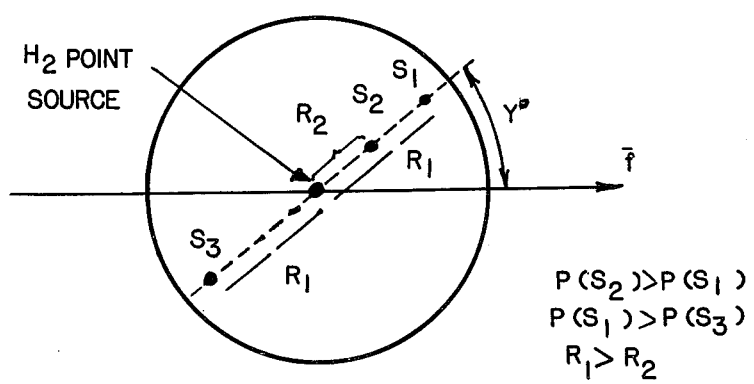
FIG. 14 is a schematic representation of an alternative probe arrangement.

From this equation, a value for the effective diffusion coefficient, D* is calculated; the sensor determines P, R is known as the distance between sensor and generator and Q is the chosen H$_2$ production rate. By rotating the electrode a known amount around the sensor and determining a new P, a value for $\bar{f}$ can be calculated with Equation 4. This process is unnecessary if a three point sensor probe is used. In this case, values for $\bar{f}$, D*, and a directional cosine $\gamma$, can be determined immediately by referring to FIG. 14 and using Equations 7, 8, 9.

$$D^* = Q/P_1 4\pi R_1 e^{R_1 \eta/(R_2 - R_1)} \text{ where } \eta = \ln(P_1 R_1/P_2 R_2) \quad (7)$$
$$\text{and } P_2 > P_1; R_1 > R_2$$

$$\cos \gamma = 1/(1 - \psi) \quad \text{where } \psi = 2(\ln(4\pi D^* R_1 P_1/Q))/\theta \quad (8)$$
$$\text{and } \theta = \ln(P_1/P_3); P_1 > P_3$$

$$\bar{f} = \theta D^*/R_1 \cos \gamma \quad (9)$$

Equation 5 is used by the device to adjust the response of the computer controller. The computer controller calculates the generation rate required to maintain the steady state. The rate and magnitude of the computer's response depends upon the characteristics of the tissue which can be closely approximated by the terms $\theta$ and $\tau$ determined from Equation 5. The controller is adjusted if continuous measurements are desired.

Development of Lumped-Parameter Model

Figure 13:
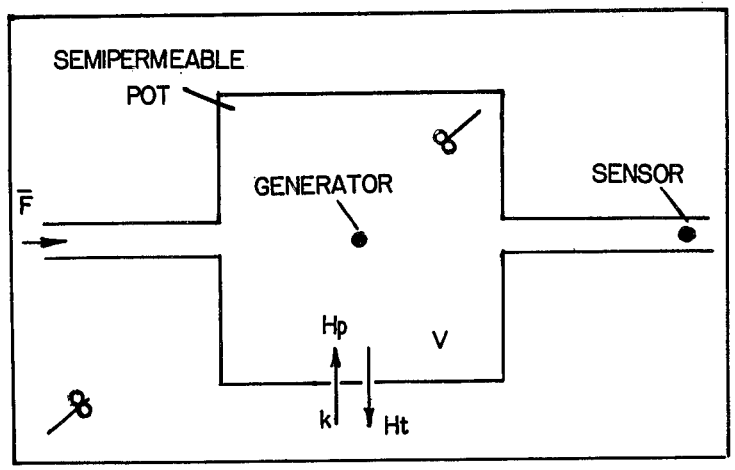
FIG. 13 is a diagram useful in explaining a practical model of the system.

The derivation of an alternative mathematical model using a lumped-parameter approach which results in a direct relationship between the H$_2$ generation rate, G(t) and a perfusion quantity F whose units are length$^3$/time is presented below with reference to FIG. 13. The tissue-generator-sensor system is modeled using a "semipermeable stirred pot with a transportation lag." The "pot" surrounds the generation site while the transportation lag refers to the time required for H$_2$ to appear at the sensor after it was formed at the generating site. The concentration of H$_2$ within the "pot," as measured by the sensor, is assumed uniform throughout the volume, V, of this "pot" by virtue of an assumption of perfect continuous stirring. The mass balance relationship describing the concentration of H$_2$ within this "pot" is expressed by equation 10.

$$V(dHp/dt) + kHp + FHp - kHt = G(t-\theta) \quad (10)$$

where
- V = volume of "semi-permeable pot" (length$^3$)
- $H_p$ = concentration of $H_2$ in the "pot" as measured by sensor site (mass/length$^3$)
- $H_T$ = concentration of $H_2$ surrounding the "pot" (mass/length$^3$)
- G(t) = generation rate of $H_2$ in the "pot" (mass/time)
- F = mean flow through "pot" (length$^3$/time)
- k = loss coefficient relating quantity of $H_2$ lost through walls of pot; (length$^3$/time) assumed a function of temperature only
- $\theta$ = transportation lag Equation 10 can be rewritten as $$\frac{dHp}{dt} + \frac{K}{V}*Hp - \frac{k}{V}Ht = \frac{G}{V}(t-\theta) \quad (2)$$

where $K^* = k + F$ and will be referred to as the "effective loss coefficient."

At some time, t∞, after the generator is turned on a steady-state concentration of $H_2$ within the pot results. Then dHp/dt = 0 and Equation 2 becomes $$K^*Hp - kHt = G(t-\theta) \quad (11)$$

Equation 11 can be simplified by assuming that $H_T$ is small. This assumption is arrived at by realizing that the "pot" is small and is surrounded by a very large sink whose concentration of $H_2$ is approximately zero, thus and Equation 12 results:

$$Hp = \frac{G(t-\theta)}{K^*} \quad (12)$$

If this steady-state concentration $H_p$ is "clamped" by varying G(t), we observe a direct relationship between G and $K^*$, viz:

$$G(t-\theta)_i/K^*_i = G(t-\theta)_{(i+1)}/K^*_{(i+1)} \quad (13)$$

and since $K^* = k + F$, a direct relationship exists between G and F. The loss coefficient, k, represents a constant offset.

Equation 13 demonstrates a direct relationship between generation rate and a loss term. Equation 13 claims that G(t) is directly related to F because of the simple form of the relationship between $K^*$ and F.

The time dependent solutions of Equations 3 and 2 have been determined to be Equations 14 and 15, respectively.

$$P(t) = \frac{Qe^{\bar{x}\bar{f}/2D*}}{8(\pi D^*)^{3/2}} \int_O^t \frac{e^{-(R^2+(\bar{f}\tau)^2)/4D*\tau}}{\tau^{3/2}} d\tau \quad (14)$$

Equation 14 was determined using the technique presented by Carslaw and Jaeger.

$$Hp(t) = \frac{\tau}{V} Gu(t-\theta)(1 - e^{-(t-\theta)/\tau}) \quad (15)$$

where $\tau = V/K^*$ and $u(t-\theta)$ is the unit step function.

Figure 11:
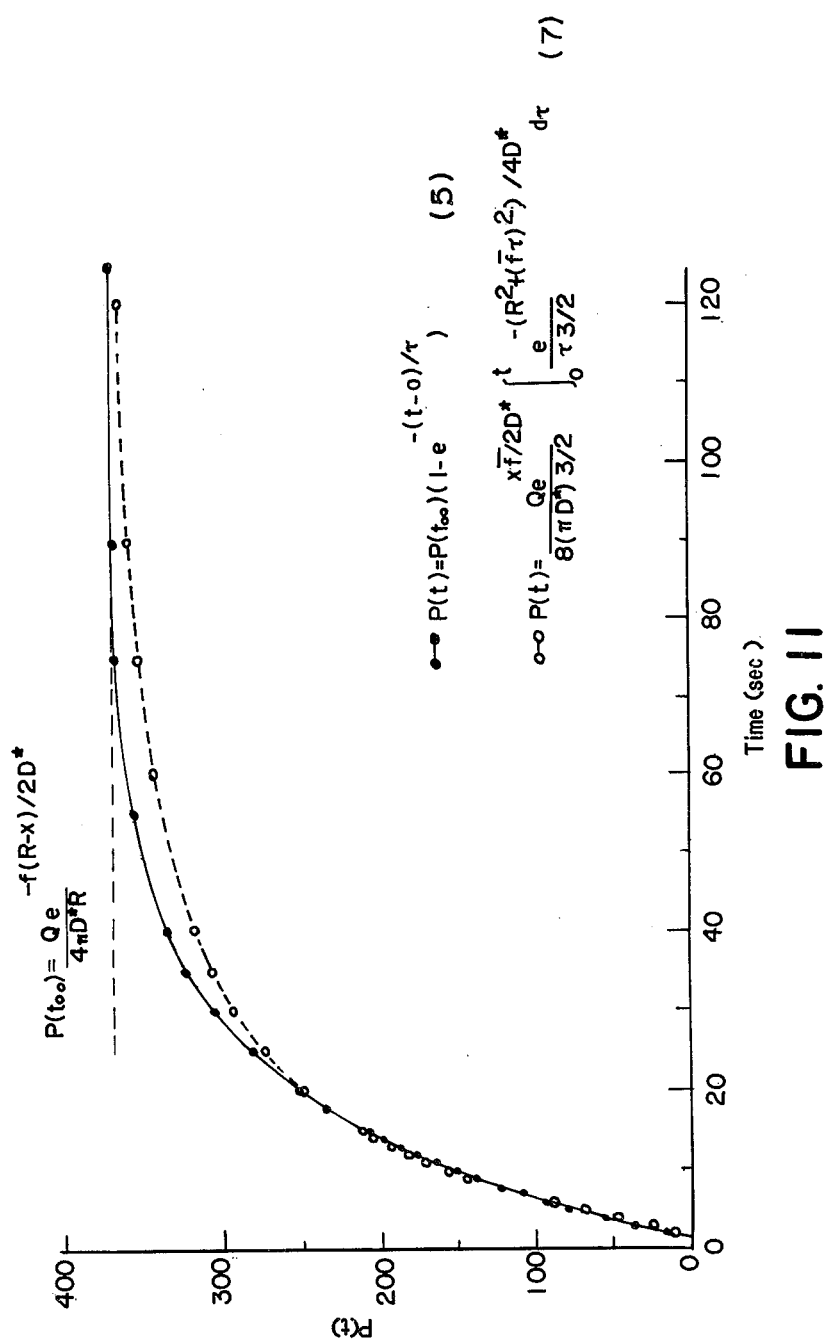
FIG. 11 illustrates the relative accuracy of a practical mathematical model with respect to a more intricate and less useful theoretical model for tissue perfusion.

Equation 14 was used to compute the time course of P(t), shown in FIG. 11, using values for $D^*$, $\bar{f}$, R, and X determined by Grossman. It is noted that $\bar{f}$ is the mean perfusion velocity vector as opposed to f which is the actual perfusion at a given point. The intergral portion of Equation 14 was computed using Simpson's rule for numerical integration.

It can be shown that Equation 15 may be written as follows:

$$P(t) = P(t\infty)(1 - e^{-(t-\theta)/\tau}) \quad (5)$$

Using Equation 4 to compute P(t∞). and the values of P(t) determined from Equation 14 values for $\tau$, the time constant, and $\theta$, the delay, were determined. A second time course of P(t) was computed using Equation 5. These values of P(t) were plotted on FIG. 11. The agreement between these curves is apparent for the first twenty seconds. After this time, moderate disagreement results: Equation 5 approaches equilibrium faster than Equation 14.

The reasonable agreement between results of the lumped parameter model with the distributed parameter model indicates that the simplest model has merit in the measurement of tissue perfusion.

The measurement of a single value of perfusion using the $H_2$ clamp device is outlined below:

1. Insert probe containing generator and sensor points into tissue; then insert reference probe in tissue at another location.
2. Select a generation rate (typically 500-1000 nanoamps a maximum value depending on the tissue) then turn both the generator and sensor on.
3. Sample and store the sensor's values for the buildup of $H_2$. When the signal no longer changes, steady-state is reached.
4. If a single sensor probe is used slowly rotate sensor around generator until the maximum value for $H_2$, P max, is observed. Now using Equation 6 calculate $D^*$, then again rotate sensor a known amount, measure $H_2$ concentration and determine $\bar{f}$ with Equation 4. For multi-sensor probe record all values, then select values according to requirements of Equations 7, 8, and 9 and compute $\bar{f}$ directly.

The $H_2$ clamp device is capable of continuous qualitative measurements of perfusion. It can be shown that the generation rate for $H_2$ reflects changes in $D^*$, the effective diffusion coefficient, which can be observed by monitoring changes in the generation rate of $H_2$ needed to maintain a constant concentration of hydrogen at the sensing electrode. $D^*$ depends upon f and the geometry of a tissue-capillary network. This geometry is usually unknown (Indeed the only way to know it is by surgery or other anatomical procedure which would defeat the purpose and advantage of the invention). Thus the exact nature of the relationship between $D^*$ and f is unknown. However, as a result of the relationships discussed above, changes in Q must reflect changes in $\bar{f}$. To observe $\bar{f}$ continuously and qualitatively one uses a single sensor probe, such as that illustrated in FIG. 7 or FIG. 9, and repeats steps 1 to 3, above, and then performs the following steps 5 and 6.

5. Store the steady-state value of $H_2$. This value will become the reference value used in the feedback control scheme. It is note that the selection of this reference value is of importance. Specifically, depending upon the tissue involved, the maximum current for hydrogen generation may be in the order of two to three microamps. Thus if a value of hydrogen generation selected is very close to the maximum value for the particular tissue concerned, the controller will have to increase the generation of hydrogen in response to the changes in perfusion. The range through which perfusion may be measured is limited by the maximum value at which the rate of hydrogen generation can be set. Thus, if a wide range is anticipated, it is advantageous to pick a mid range level of hydrogen generation as a starting point in order to have a relatively wide range for up and down variations in perfusion. On the other hand, if too low a value is selected and the range is not used, the user of the process will receive measurements which are not as accurate as can be obtained using higher values of hydrogen generation. Determine the values of time response and the delay by performing a regression analysis on the stored points. Using these values and appropriate well known tuning relationships, determine the controller parameters.

6. Turn on the controller. The controller will vary Q in the appropriate magnitude and direction to maintain the reference value constant. Changes in $\bar{f}$ will change the steady-state $H_2$ value. The controller responds to these concentration changes by altering Q. Changes in Q will qualitatively reflect changes in $\bar{f}$.

Continuous quantitive measurement is possible if Equation 5 is used, however, values for F will result. It can be shown that following steps 1 to 3, 5, 6 above will yield a direct linear relationship between Q and F.

While an illustrative embodiment of the invention has been described, it is, of course, understood that various modifications may be made to the disclosed apparatus by those skilled in the art. For example, an alternative method may be used for the introduction of hydrogen into the system. This may be achieved, especially in non-physiological uses (i.e. measuring perfusion in a subteranian formation) by introducing hydrogen through a capillary tube and metering the hydrogen emitted. Likewise, other materials, such as oxygen or chlorine may be used as tracers instead of the hydrogen disclosed. Similarly, the digital feedback control network disclosed may be replaced by an analog device. Such modifications as would be obvious to those of ordinary skill in the art are within the spirit and scope of the invention which is limited and defined only by the appended claims.

I claim:

1. Apparatus for measuring the perfusion rate of fluid through animal tissue comprising probe means adapted to be contacted with the tissue to be measured for generating a detectible substance, such as hydrogen, in situ in said tissue responsive to an applied electrical current, first sensor means spaced a first distance from such probe means adapted to be contacted with said tissue for sensing the concentration of said substance, control means operatively associated with said sensor means for applying a current to said probe means at a value to maintain the concentration of said substance at said first sensor means at a selected level, and measuring means for determining the value of electrical current required to be applied to said probe means to maintain the concentration of said substance at said first sensor means at said selected level whereby the perfusion rate may be determined as a function of the value of said current.

2. Apparatus in accordance with claim 1 and including additional sensor means in predetermined spaced relation to said probe means for determining the concentration of said substance at a position or positions displaced from said first sensor means, means for determining the diffusion rate of said substance through said tissue as a ratio of the substance concentrations sensed by said one sensor means and said additional sensor means, and means for subtracting the diffusion rate from said perfusion rate, thereby to determine the flow rate through said tissue.

3. Apparatus in accordance with claim 2 and including four said sensor means, said sensor means being positioned essentially in a straight line.

4. A method of measuring the perfusion rate of fluid through animal tissue comprising the steps of contacting an electrode probe with the tissue to be measured, contacting at least one sensor probe with said tissue at a predetermined spaced position from said electrode probe, applying an electrical current to said electrode probe, thereby to cause a gaseous substance detectible by said sensor probe to be continuously generated in situ in said tissue, varying the quantum of current applied at said electrode probe to a value required to maintain the concentration of said substance at said sensor probe at a selected level and determining the perfusion rate as a function of the quantum of current required to be applied to said electrode probe to maintain said concentration at said sensor probe at said selected level.

5. A method in accordance with claim 4 and including the steps of contacting an additional sensor probe or probes with said tissue in predetermined spaced relations to said at least one sensor probe, determining the diffusion rate of said substance through said tissue as a function of the measured concentrations of said substance at said at least one and said additional probes, and subtracting said diffusion rate from said perfusion rate to derive the flow rate of fluid through said tissue.

6. The method in accordance with claim 5 wherein said sensor probes are four in number, said probes being aligned essentially in a straightline, and derive said flow rate by selected readings at three of said four sensor probes which satisfy the conditions $P(S_2) > P(S_1)$ and $P(S_1) > P(S_3)$, where $P(S_1)$ is the concentration of said substance at one of said three sensor probes, $P(S_2)$ is the concentration of said substance at another of said three sensor probes, and $P(S_3)$ is the concentration of said substance at the third of said three measurement devices.

* * * * *